United States Patent
Lazarus et al.

(10) Patent No.: US 6,749,852 B1
(45) Date of Patent: Jun. 15, 2004

(54) METHOD FOR PREVENTING AND INHIBITING HUMAN HLA ALLOIMMUNE RESPONSE TO PLATELET TRANSFUSION

(75) Inventors: Alan H. Lazarus, Toronto (CA); John Freedman, Toronto (CA); Andrew R. Crow, East York (CA)

(73) Assignee: Canadian Blood Services, Ontario (CA)

( * ) Notice: Subject to any disclaimer, the term of this patent is extended or adjusted under 35 U.S.C. 154(b) by 0 days.

(21) Appl. No.: 09/709,249

(22) Filed: Nov. 10, 2000

Related U.S. Application Data

(60) Provisional application No. 60/164,777, filed on Nov. 12, 1999.

(51) Int. Cl.⁷ .............................................. A61K 39/395
(52) U.S. Cl. ................................ 424/141.1; 424/152.1; 424/153.1
(58) Field of Search ........................... 424/141.1, 152.1, 424/153.1; 514/885

(56) References Cited

PUBLICATIONS

Webster's 9th New Collegiate Dictionary p. 933, 1990.*
Shalit et al. J Clin Micro 22(5):877–879, 1985.*
Damjanovich et al. PNAS, USA 92:1122–1126, 1995.*
Andrew R. Crow et al., *British Journal of Haematology*, Antibody–mediated inhibition of the human alloimmune response to platelet transfusion in Hu–PBL–SCID mice, 1999, 104, pp. 919–924.

* cited by examiner

*Primary Examiner*—G. R. Ewoldt
(74) *Attorney, Agent, or Firm*—Nixon Peabody LLP

(57) ABSTRACT

The present invention relates to a method for preventing HLA alloimmune response to platelet transfusion. The method comprises the step of presensitizing platelets with at least one monoclonal HLA antibody. The platelets if administered to a patient prevent an HLA alloimmune response from said patient.

3 Claims, 4 Drawing Sheets

METHOD FOR PREVENTING AND INHIBITING HUMAN HLA ALLOIMMUNE RESPONSE TO PLATELET TRANSFUSION

This application claims the benefit of priority of U.S. Provisional App. No. 60/164,777, filed Nov. 12, 1999.

BACKGROUND OF THE INVENTION (a) Field of the Invention

The invention relates to a method for preventing and/or inhibiting HLA alloimmune response to platelet transfusion, by presensitizing platelets with at least one monoclonal HLA antibody.

(b) Description of Prior Art

Many patients who receive platelet transfusions become alloimmunized, rendering them refractory to subsequent platelet transfusions. It is thought that "contaminating" HLA Class II bearing antigen presenting cells (APC) augment the production of these alloantibodies and various methods have been used to inactivate or remove these "contaminating" cells, including the use of ultraviolet radiation and leucofiltration. Although these methods have been successful at reducing the incidence of primary alloimmunization, many multi-transfused patients still become alloimmunized. For those patients already alloimmunized by prior transfusion or pregnancy, even leucodepleted platelets can stimulate a secondary alloimmune response. Animal studies suggest that extreme leucodepletion may be detrimental to inhibiting immune responses to transfusions, suggesting that the ability of leucodepletion to decrease alloimmunization may have reached its threshold.

Antigen-specific IgG, when injected at the time of antigen exposure, can induce a strong suppression of the immune response. The immunosuppressive effect is particularly effective with large antigen systems, such as red blood cells, and this is currently applied to the prevention of fetal erythroblastosis in Rh negative women by administration of anti-D IgG. Pretreatment of whole blood with polyclonal alloantisera has been shown to prevent alloantibody production in rat models of transfusion. More refined studies in rats have shown that pretreatment of platelets or leukocytes with alloantisera also inhibits the alloimmune response to platelet transfusion.

Antibody/antigen complexes can inhibit immune responses and it has been hypothesized in the immunological literature that this down-regulation of humoral responses is likely contributed to by a negative feedback pathway mediated by B cell Fcγ receptor (FcγR) co-crosslinking with the B cell Ig receptor (BCR), resulting in the B cell entering a "non-responsive" state mediated by activation of a negative feedback pathway at the level of BCR signaling.

An alternate theory developed is that alloimmune serum from alloimmunized individuals contains elevated levels of an anti-IgG (i.e. an IgG rheumatoid factor (RF)) and this IgG RF contributes to or mediates a decrease in the alloimmune response. Purified IgG RF from the serum of alloimmunized rats exerts immunosuppressive effects in vivo and in vitro.

The inventors have shown previously that SCID mice, engrafted with human (Hu) peripheral blood lymphocytes (PBL) from alloimmunized donors are a valuable tool for studying alloimmunization and that transfusion of these Hu-PBL-SCID mice with human alloimmune sera presensitized platelets results in a decreased alloantibody response to further untreated platelet transfusions (Crow A R, et al., Br J Haematol 104:919, 1999).

In the present invention, a single dose of platelets presensitized with monoclonal HLA Class I antibody (either depleting or non-depleting) abrogated the alloantibody response to five subsequent untreated platelet challenges. FCR mediated B cell down regulation was not required for the alloimmune inhibition observed, since F(ab')2 fragments of monoclonal anti-HLA-A,B,C antibody completely abrogated the immune response whereas platelets treated with platelet-specific antibody or control murine IgG had no inhibitory effect.

It would be highly desirable to be provided with a new approach for inhibiting the human alloimmune response to platelet transfusion.

SUMMARY OF THE INVENTION

One aim of the present invention is to provide a new approach for inhibiting the human alloimmune response to platelet transfusion.

In accordance with the present invention there is provided a new method for inhibiting the human alloimmune response to platelet transfusion.

Since monoclonal antibodies can be made by recombinant means and the fine specificity of the antibody is not critical to inhibit alloimmunization, the present invention provides a new and practical approach for inhibiting the human alloimmune response to platelet transfusion.

In accordance with the present invention there is provided a method for preventing HLA alloimmune response to platelet transfusion, comprising the step of presensitizing platelets with at least one monoclonal antibody against HLA, a portion thereof, or β2-microglobulin, wherein the platelets if administered to a patient prevent an HLA alloimmune response from the patient.

The monoclonal antibody can be for example W6/32, L368, and MA2.1 ATCC accession numbers HB-95, HB-149, and HB-54, respectively wherein such antibodies are readily available without restrictions from the American Type Culture Collection (ATCC).

In accordance with the present invention there is also provided a method for inhibiting an HLA alloimmune response to platelet transfusion. The method comprises the steps of:

a) presensitizing platelets with at least one monoclonal antibody against HLA or a portion thereof; and b) transfusing with the presensitized platelets of step a) to a patient, the presensitized platelets inhibiting an HLA alloimmune response from the patient. The HLA alloimmune response can still be prevented after at least two transfusions from the patient.

The term "platelets" in the instant application is intended to also include, without limitation, platelet concentrates, platelet substitutes, platelet rich plasma, platelet poor plasma, lyophilized platelets, platelets fragments, red blood cells, red blood cell concentrates, leukocytes and buffy coats.

The monoclonal antibodies useful in the method of the present invention include, without limitation, monoclonal antibodies against either Public or Private epitopes of HLA. The monoclonal antibodies do not have necessarily to be against HLA as monoclonal antibodies against the $β_2$-microglobulin ($β_2$M) portion of HLA are also effective at alloimmune inhibition.

The expression "monoclonal antibodies" also meant to include without limitation murine monoclonal antibodies, recombinant MAbs, humanized MAbs, single chain MAbs, bispecific MAbs where one epitope is HLA or $\beta_2M$, F(ab)'$_2$ and F(ab) fragments of these monoclonal antibodies.

The present invention can be used to protect or prevent alloimmunization. However, the method of the present invention can also be used for preventing refractoriness to subsequent transfusions in alloimmunized patients.

In accordance with the present invention, there is provided a method for preventing refractoriness to subsequent transfusions in an alloimmunized patient, comprising a) presensitizing platelets with at least one monoclonal antibody against HLA or a portion thereof, and b) transfusing the alloimmunized patient with the presensitized platelets of step a), the presensitized platelets preventing refractoriness to the transfusion.

In accordance with the present invention, there is provided a method for preventing an alloimmune disease or an alloresponse. The method comprises the steps of a) presensitizing platelets with at least one monoclonal antibody against HLA or a portion thereof; and b) transfusing with the presensitized platelets of step a) to a patient. The presensitized platelets inhibit an HLA alloimmune response from the patient.

The alloresponse may be for example an organ transplantation-related complication, such as an organ rejection.

DETAILED DESCRIPTION OF THE INVENTION

Figure 1:
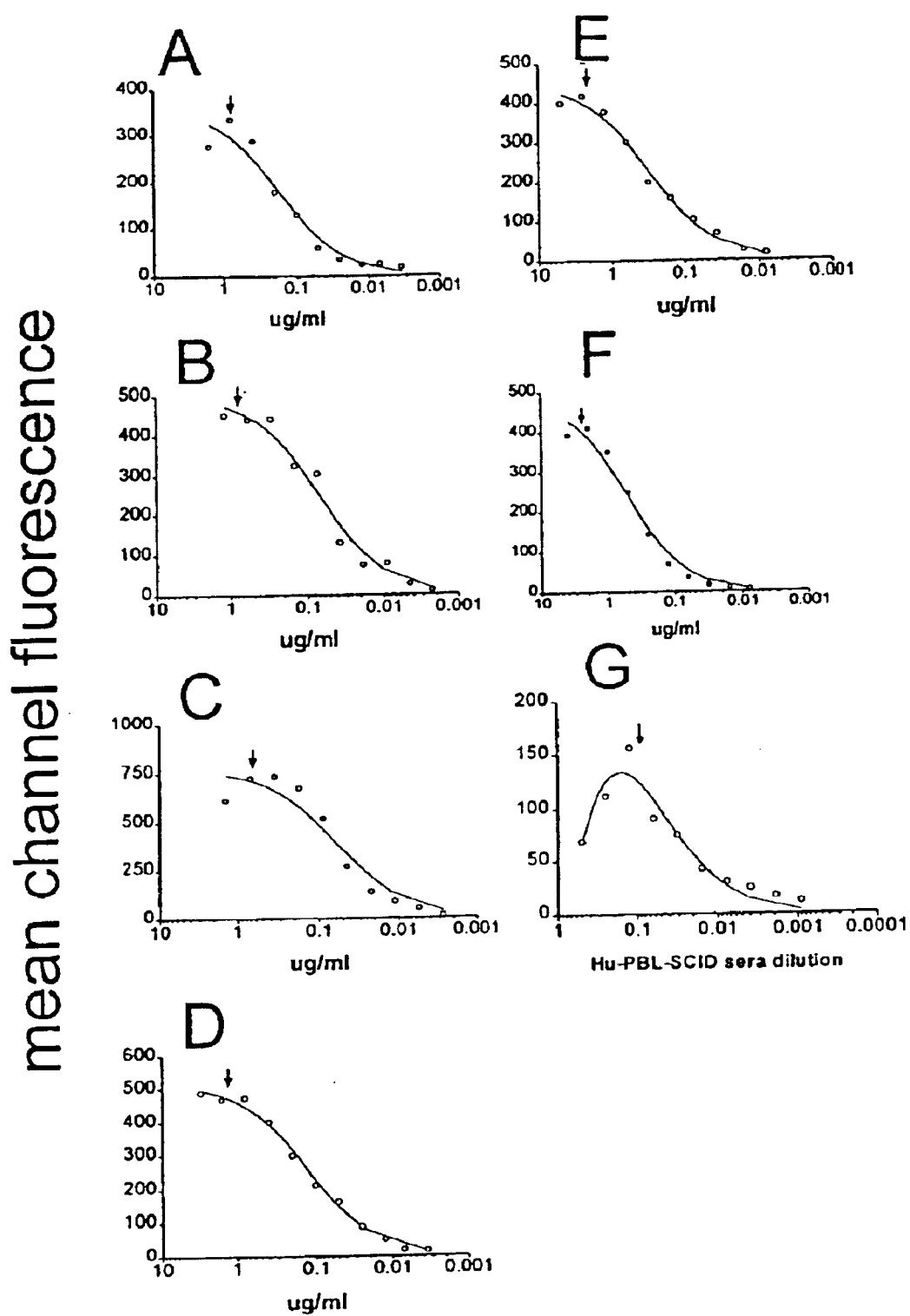
FIGS. 1A to 1F are graphs illustrating saturation of transfused platelets by monoclonal antibodies.
FIG. 1G is a graph illustrating saturation of alloantibody-containing Hu-PBL-SCID sera.

Previous results have shown that presensitization of donor platelets; white blood cells or whole blood with allo-specific IgG results in a diminished immune response against subsequent transfusions of platelets. To better understand the mechanism of how alloantibody presensitization results in a decreased alloimmune response, and since monoclonal antibodies do not contain contaminants as do polyclonal antibody preparations, the allospecific inhibition in the absence of the effect of the inhibitory IgG(s) can thus be examined in the present application. Murine monoclonal antibodies directed to polymorphic and non-polymorphic regions of human HLA as well as platelet-specific molecules were used in the present invention. Accordingly, it is demonstrated in the present application that presensitization with anti-human HLA Class I antibodies as well as $\beta_2M$-specific antibody could protect against alloantibody production to 5 subsequent untreated platelet challenges. Use of depleting (complement fixing), non-depleting, high or low FcR binding antibodies or F(ab')2 fragments of HLA-specific antibody also resulted in complete inhibition of alloantibody. This protection was not seen when the platelets were presensitized with monoclonal antibodies to CD42a (GPIX), CD32 (low affinity IgG-Fc$\gamma$ receptor) or murine IgG; thus, this inhibition was therefore antigen specific and independent of complement-fixation or antibody-mediated Fc receptor dependent immunoregulatory effects. This inhibition was not dependent on HLA fine specificity, since antibodies directed at the $\beta_2M$ portion of HLA class I were as effective as antibodies against any of the HLA-$\alpha$ regions (either polymorphic or non-polymorphic regions) of class I. In accordance with the present invention, a single regime of HLA Class I specific monoclonal antibody presensitized platelets completely inhibits alloimmunization to further transfusions and offers an approach to preventing alloimmunization.

Monoclonal HLA-A2 Antibody-treated Platelets Inhibit Alloantibody Production

Previous work showed that human polyclonal alloantisera to HLA-A2 could decrease production of alloantibody to HLA-A2 antigen (Crow A R, et al., *Br J Haematol* 104:919, 1999). To determine if a monoclonal antibody could achieve the same effect, the inventors employed a murine monoclonal antibody (MA2.1), specific for HLA-A2 (see Table 1).

TABLE 1

Characteristics of Sensitizing Antibodies

| Antibody | Subclass | Specificity | Complement fixing | Fc$\gamma$RII Binding[1] | Epitope |
|---|---|---|---|---|---|
| W6/32 | IgG$_{2a}$ | HLA-A,B,C | + | + | $\alpha2/\alpha3$ |
| MA2.1 | IgG$_1$ | HLA-A2 | − | + + + + | $\alpha1$ |
| L368 | IgG$_1$,k | $\beta_2$ M | − | + + + + | $\beta_2M$ |
| IV.3 | IgG$_{2b}$ | CD32 (Fc$\gamma$RII) | + | + + + | — |
| AN51 | IgG$_{2a}$,k | CD42a (GPIX) | + | + | — |

[1]Fc$\gamma$RII binding of murine IgG, highest to lowest affinity: IgG1, 2b>>2a, 3

Hu-PBL-SCID mice were successfully engrafted as determined by the presence of human IgG in serum. Mice engrafted with human lymphocytes from an HLA-A2 alloimmunized donor and challenged with HLA-A2 positive platelets produced alloantibody detectable at day 7 post engraftment and increased over time to day 24 (FIG. 2, o) as compared with unchallenged mice (FIG. 2, Δ). However, when the first platelet challenge was presensitized with a saturating dose of a murine monoclonal antibody to HLA-A2 (FIG. 1A), there was no alloantibody response to 5 subsequent untreated platelet challenges (FIG. 2, ; p<0.001 at all days except day 10, p=0.02 and day 18, p=0.002). Presensitized platelets did not decrease overall IgG production in the mice (1.8±0.7 mg/ml) compared with untreated platelets (2.1±0.7 mg/ml).

Figure 2:
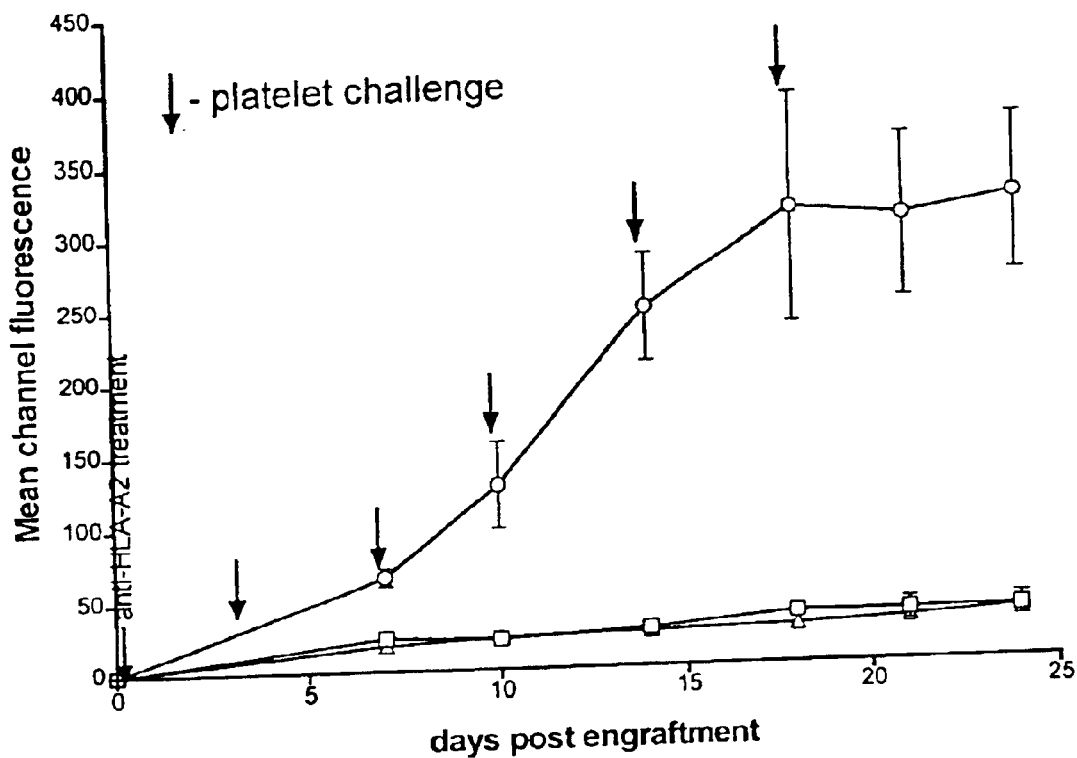
FIG. 2 is a scattergram plot illustrating inhibition of the alloantibody response by monoclonal HLA Class I antibody treated platelets.

In FIGS. 1A to 1G, platelets were incubated with serial dilutions of antibody (FIG. 1A: anti-HLA-A2, FIG. 1B: anti-HLA, FIG. 1C: anti-$\beta_2M$, FIG. 1D: anti-FcR, FIG. 1E: anti-CD42a, FIG. 1F: F(ab')2 anti-HLA). The x-axis shows antibody dilution, the y-axis represents antibody binding as assessed by flow cytometry. The arrow indicates the amount of antibody used to presensitize the platelets prior to transfusion. FIG. 1G represents the dilution of alloantibody-containing Hu-PBL-SCID sera used for alloantibody detection and blocking experiments.

In FIG. 2, SCID mice were engrafted with lymphocytes from the first donor, making HLA-A2 specific antibodies. Engrafted Hu-PBL-SCID mice were either not further manipulated (Δ), challenged twice weekly (arrow) with HLA-A2 positive platelets (o), or challenged with monoclonal HLA-A2 antibody treated platelets, followed by 5 subsequent untreated platelet challenges (□) as above. The x-axis represents days post engraftment; y-axis is alloantibody binding to HLA-A2 positive PBLs in arbitrary mean fluorescence units. Cumulative data from 2 separate experiments are illustrated, n=10 for all groups.

Monoclonal Antibodies to HLA Class I, But Not to Platelet-specific Antigens, Inhibit the Alloimmune Response Hu-PEL-SCID mice engrafted with lymphocytes from either of the two alloimmunized donors were challenged with platelet preparations presensitized with saturating doses of antibodies to HLA Class I (FIGS. 1A to 1C) and other platelet surface antigens (FIGS. 1D and 1E), followed by repeated untreated platelet challenges. Sera from the engrafted mice were analyzed at 21 days post engraftment for the presence of alloantibody. These Hu-PBL-SCID mice, when challenged with standard platelet preparations produced alloantibody as assessed by flow cytometry (FIG. 3).

Figure 3:
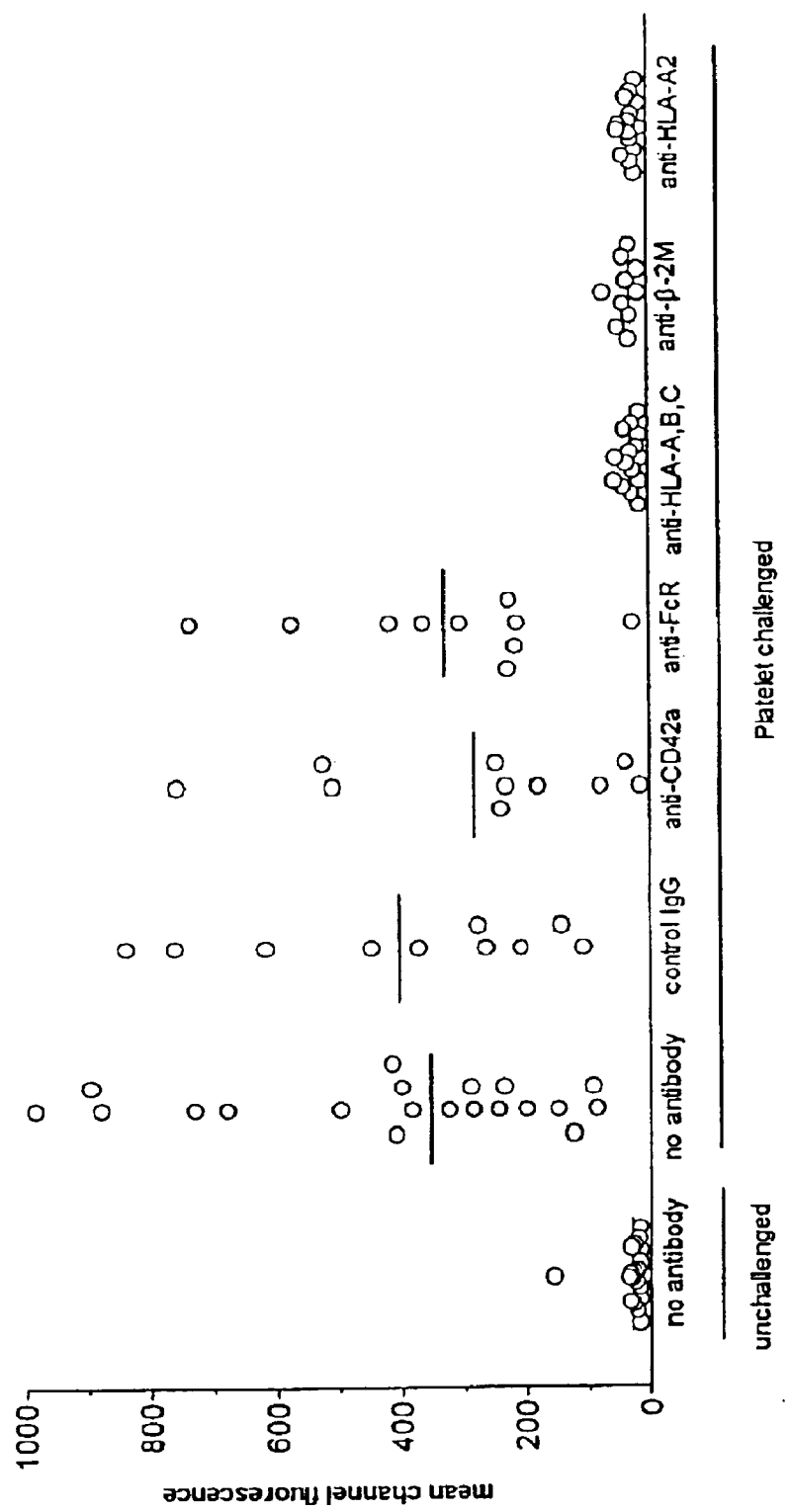
FIG. 3 illustrates the effect of monoclonal antibodies on platelet immunogenicity.

In FIG. 3, SCID mice were engrafted with lymphocytes from the HLA-A2 or polyspecific alloimmunized donor and challenged as in FIGS. 1A to 1G with HLA-A2 positive platelets or pooled platelets expressing multiple HLA alleles. Platelets were either untreated or pretreated with the monoclonal antibodies listed on the x-axis for the first challenge only. The y-axis represents alloantibody binding to target PBLs at 21 days post engraftment. The horizontal bar represents the mean fluorescence for the specified treatment groups.

Pretreatment of platelet preparations with murine IgG, CD42a-specific antibody, or FcγRII specific antibody, did not significantly decrease alloantibody production to further untreated platelet preparations compared to the positive control, untreated platelets (p=0.92 for mIgG, p=0.21 for CD42a antibody, p=0.40 for FcγR antibody). In contrast, platelets presensitized with either a monoclonal antibody to a polymorphic HLA epitope present on all HLA Class I molecules (HLA-A,B,C), a non-polymorphic epitope (HLA-A2), or the $\beta_2M$ invariant chain (Table 1), induced no alloantibody production to further untreated platelet challenges (FIG. 3; p<0.0001 for HLA-A,B,C and $\beta_2M$ antibodies; p<0.002 for HLA-A2 antibody). The total serum human IgG levels were not different in mice transfused with antibody-treated platelets compared to those receiving untreated platelets.

Alloantibody Inhibition by Monoclonal Antibodies is Not FcR Dependent

To determine if the alloantibody inhibition was associated with Fcγ R dependent effects, the first platelet challenge was either untreated or presensitized with saturating doses of whole anti-HLA antibody or a highly purified F(ab')2 fragment of the polymorphic HLA-A,B,C binding antibody (FIGS. 1B and 1F). In contrast to the untreated platelet challenge group, platelets presensitized with either whole antibody or F(ab')2 fragment failed to induce an alloantibody response to further untreated platelet challenges at 21 days post engraftment (FIG. 4; p<0.0001 for whole antibody; p=0.003 for F(ab')2 fragment). Anti-HLA antibodies were also able to inhibit alloantibody production regardless of their ability to bind host FcR (Table 1); W6/32 was as effective at alloimmune inhibition as MA2.1 or L368 All groups produced equivalent levels of overall IgG.

Figure 4:
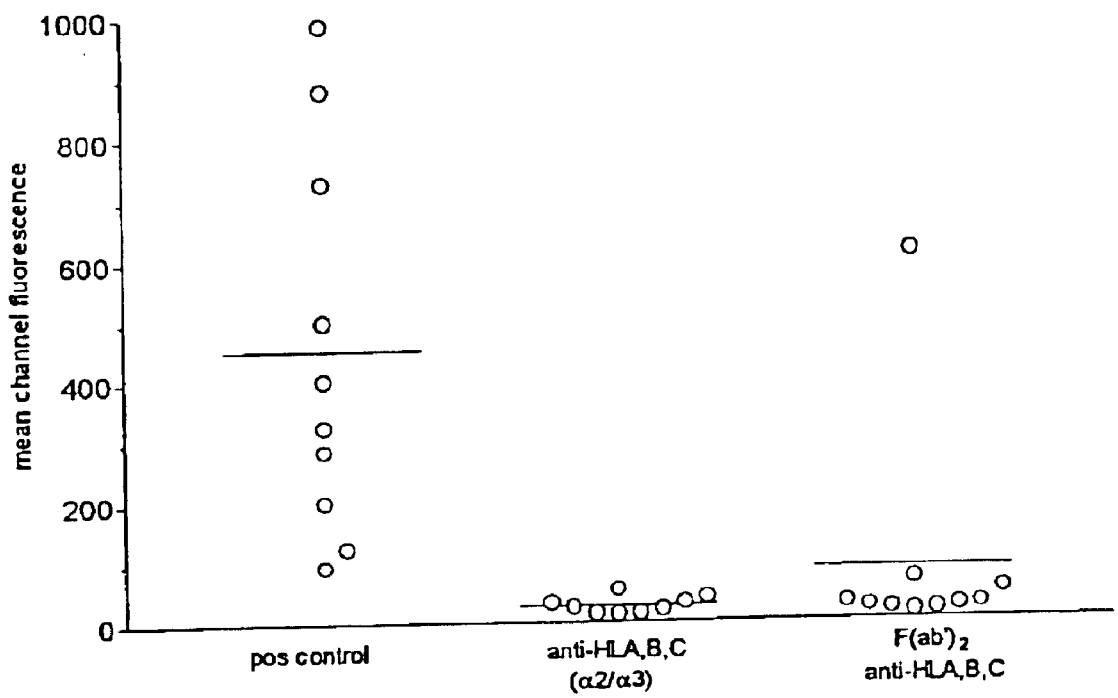
FIG. 4 illustrates the effect of F(ab')2 fragment of monoclonal antibody W6/32 on platelet immunogenicity.

In FIG. 4, mice were engrafted as in FIG. 2, and challenged with untreated platelets or platelets treated with whole or F(ab')2 fragment of W6/32 for the first challenge only.

Monoclonal HIA Class I Antibodies Do Not Sterically Hinder Binding of Human Alloantibodies The HLA-A,B,C and $\beta_2M$ monoclonal antibodies do not react with the 1 hypervariable region of HLA and would therefore not be expected to sterically hinder an immune response against HLA allo-regions. Nevertheless, these antibodies were tested as to whether or not they interfere with the binding to HLA by the allospecific sera from Hu-PBL-SCID mice and vice versa. Sera from platelet-challenged Hu-PBL-SCID mice (Table 2) and the monoclonal HLA antibodies used in these experiments (Table 3) were titrated with HLA-A2 positive PBLs and analyzed by flow cytometry to determine the minimum dose needed to saturate target cells.

TABLE 2

Inability of monoclonal HLA antibodies to block binding of human HLA antibodies

| | Pre-incubation | | |
|---|---|---|---|
| | W6/32 | L368 | MA2.1 |
| Nil | 1099 ± 561 | 1240 ± 705 | 473 ± 254 |
| allosera | 1332 ± 510 | 1336 ± 509 | 536 ± 209 |

Target cells were pre-incubated with nothing (Nil) or with monoclonal antibodies followed by incubation with Hu-PBL-SCID sera at concentrations specified in FIG. 1G and as described herein. Numbers represent mean channel fluorescence intensity±S.E.M. from 3 experiments.

TABLE 3

Inability of human alloantibodies to block monoclonal HLA antibody binding
Pre-incubation with SCID sera

| Nil | 362 ± 132 |
|---|---|
| W6/32 | 384 ± 167 |
| L368 | 557 ± 303 |
| MA2.1 | 347 ± 128 |

Target cells were pre-incubated with nothing or with Hu-PBL-SCID sera followed by incubation with monoclonal HLA antibody as described in Table 2. The values represented in Table 3 are mean channel fluorescence±S.E.M. from 3 separate experiments.

HLA-A2 positive PBLs that had been pre-incubated with a saturating concentration of alloantibody-containing Hu-PBL-SCID sera did not block the binding of the HLA-specific monoclonal antibodies (Table 2). None of the monoclonal antibodies blocked the binding of the Hu-PBL-SCID alloantibodies as measured by flow cytometry. The reverse was also true, target cells pre-incubated with HLA-specific monoclonal antibodies were still able to react with Hu-PBL-SCID alloantisera (Table 3).

Discussion

A "humanized" SCID mouse model of human platelet transfusion was used to study the effect of various monoclonal anti-HLA antibodies on alloimmunization. Whereas the transfusion of untreated platelets induced high levels of alloantibody, platelets presensitized with monoclonal HLA antibodies, but not platelet-specific antibodies, induced virtually no alloantibody in response to five untreated platelet transfusions. The HLA fine specificity of these antibodies and their ability to fix complement did not correlate with the inhibition of the alloimmune response in the model used for the present invention.

Immune modulation by antigen specific polyclonal IgG has been well documented and is thought to occur by means of crosslinking B cell surface Ig with Fc receptors, resulting in the down-regulation of antibody responses. This type of immune regulation requires intact IgG. Antigen-specific polyclonal antibodies have been successfully employed to inhibit a variety of immune responses, including large systems such as red cells as well as viruses and bacterial antigens (Crow AR, et al., *Br J Haematol* 104:919, 1999). Antigen/antibody complexes have been shown to negatively regulate B cell responses by co-crosslinking surface antigen receptors with Fc receptors. This mode of immune suppression has been used clinically to prevent hemolytic disease of the newborn by administration of anti-D IgG to Rh negative women. The ability of these monoclonal HLA antibodies to negatively regulate B cell antibody production via this negative feedback mechanism is not required for the inhibition seen in the present invention.

Transfusion experiments in rats and Hu-PBL-SCID mice (Crow AR, et al., *Br J Haematol* 104:919, 1999) have demonstrated that injection of platelets presensitized (IgG coated) with polyclonal sera reactive with the hypervariable ($\alpha_1$ domain) region of MHC class 1 could prevent alloimmunization to further transfusions. In the rat models of blood transfusions, the inhibition was linked to cell antigen specific antibodies resulting in FcR-mediated B cell immune suppression or to contamination with an anti-IgG rheumatoid factor-like antibody also resulting in B cell inhibition. In the present invention, it is demonstrated through the use of F(ab')2 fragments of anti-HLA-A,B,C, that the Fc portion of IgG was not required for the alloimmune inhibition. Since the Fc portion of IgG is necessary for co-crosslinking FcR and the BCR, the immune modulation seen here is independent of B cell FcR mediated down-regulation. Also, platelets presensitized with monoclonal antibody to CD32 and CD42a did not result in a decrease in anti-HLA alloantibody production, as would be expected if this immune modulation was due to down-regulation of B cells by FcR crosslinking with the platelet/antibody complexes. Furthermore, the anti-HLA antibodies were equally effective at inhibiting the alloimmune response to further transfusions regardless of their ability to bind host FcR.

Antibody-coated cells are susceptible to complement-mediated lysis or clearance by the reticuloendothelial system. While the W6/32 (HLA-A,B,C) antibody is complement-fixing, the antibodies MA2.1 (HLA-A2) and L368 ($\beta_2$M) are not, and thus complement-dependent platelet clearance is not the mechanism for the immunosuppression observed. Furthermore, the platelet-specific antibodies are complement-fixing as well, and mice challenged with these treated platelets induced a strong anti-HLA alloantibody response to further untreated platelet transfusions. Also, only the first platelet challenge was treated with the monoclonal antibodies, all subsequent transfusions being with untreated platelets.

The monoclonal HLA-specific antibodies might have blocked the epitopes on Class I to which the patients are immunized, in effect "masking" the HLA Class I on the transfused platelets from the reticuloendothelial system (RES) of the Hu-PBL-SCID mice. The HLA-specific monoclonal antibodies did not down-modulate HLA Class I expression and did not block the binding of anti-HLA alloantisera from Hu-PBL-SCID to target cells. Nor did alloantisera block the binding of the monoclonal antibodies to platelets. Nonetheless, presensitization of platelets with HLA antibodies may allow the platelets to go undetected by the host immune system and thus prevent an immune response. This may explain why challenge with untreated platelets after the first exposure to pretreated platelets did not elicit an antibody response.

Although leucodepletion may prevent primary alloimmune responses to platelet transfusions, it is not completely effective and may not be able to prevent further alloimmunization. Antibody-mediated inhibition of the human alloimmune response may provide a useful regime for inhibiting the incidence of alloimmunization to platelet transfusions.

The present invention will be more readily understood by referring to the following examples, which are given to illustrate the invention rather than to limit its scope.

EXAMPLE 1

Murine Monoclonal Antibodies

The hybridomas W6/32 ($IgG_2a$, anti-HLA-A,B,C), MA2.1 ($IgG_1$, anti-HLA-A2/B17), L368 ($IgG_1k$, anti-$\beta_2$ microglobulin), and IV.3 ($IgG_{2b}k$, anti-Fc$\gamma$RII) were obtained from A.T.C.C. (Manassas, Va.). Antibodies were used as tissue culture supernatants. The monoclonal anti-CD42a (AN51, $IgG_{2a}k$) was obtained from Dako Diagnostics (Mississauga, ON). The control murine IgG was purchased from Cedarlane (Hornby, ON).

The F(ab')2 fragment of W6/32 was prepared by incubating 2 mg/ml purified antibody in 0.2M acetate buffer (pH 4.5) with 0.1 mg/ml pepsin for 20 h at 37° C. Digestion was stopped by the addition of 2M Tris base. Free Fc fragments and whole IgG were removed by passage of the digested product through a Protein-A Sepharose™ column. F(ab')2 purity was found to be >99% by gel scanning and it was again passed over Protein-A Sepharose™ to remove the remaining 1% contaminants. The ability of the F(ab')2 fragments to bind platelet HLA was confirmed by flow cytometry (FIG. 1F).

EXAMPLE 2

SCID Mice

C.B.17 SCID female virgin mice (6–10 weeks of age) were obtained from Charles River Laboratories (Montreal, PQ) and were housed under gnotobiotic conditions in the St. Michael's Hospital research vivarium. Blood from the tail vein (300 $\mu$l) was collected into untreated microvette tubes (Sarstedt, Montreal, PQ). Serum was separated after incubation at 22° C. for 2 h. Serum levels of endogenous murine IgG were determined by ELISA and mice with a serum level of greater than 10 $\mu$g/ml were excluded from the study.

EXAMPLE 3

Reconstitution of SCID Mice

PBL were obtained by Percoll separation of whole blood from female blood donors with stable, low levels of circulating HLA Class I alloantibodies due to prior pregnancy. The first donor was blood group O, HLA-A1, A3, B7 and B37 positive and had circulating anti-HLA-A2 and -B5 alloantibodies. The second donor was blood group A, and circulating levels of broad polyspecific alloantibodies. All SCID mice were injected with 20 $\mu$l of anti-asialo $GM_1$ antiserum (Wako Pure Chemical Industries Ltd., Dallas, Tex.) 1 day prior to reconstitution and were exposed to 200 cGy of $\gamma$-irradiation just prior to reconstitution to enhance cellular engraftment as previously described. Human PBL ($1 \times 10^7$/mouse) were isolated and injected into the peritoneal cavity as previously described (Crow A R, et al., *Br J Haematol* 104:919, 1999).

EXAMPLE 4

Reconstituted SCID Mouse Challenge

Challenge platelets were obtained from buffy coats in CP2D bags and isolated by centrifugation of the platelet-rich plasma at 200 x g. Hu-PBL-SCID mice were challenged with $\gamma$-irradiated (2,500 cGy) human platelets from five random HLA-A2 positive donors with or pooled platelets from five random donors with different Class I alleles. The first challenge consisted of 4×10⁸ platelets/mouse (equivalent to 2 transfusions in a human). Subsequent challenges were with 2×10⁸ untreated platelets (equivalent to 1 human transfusion), twice weekly for three weeks. In specified groups of mice, the platelets used for the first challenge consisted of platelets presensitized with saturating levels of monoclonal antibody (as assessed by flow cytometry; FIGS. 1A to 1G), or 1 µg/ml control murine IgG, for 0.5 h at 22° C. Platelets were then washed twice with phosphate buffered saline (PBS; pH 7.2) and resuspended in PBS. Mice that received antibody-sensitized platelets only did so on the day of engraftment; the five subsequent transfusions were with untreated platelets.

EXAMPLE 5
Antibody Detection

Mouse and human serum IgG levels were assessed by ELISA. Alloantibodies were detected by flow cytometry as previously described (Crow A R, et al., *Br J Haematol* 104:919, 1999). Briefly, sera from Hu-PBL-SCID mice were diluted 1:10 in PBS and incubated with 2×10⁵ pooled lymphocytes (obtained from the same source as the platelet challenges). The cells were then washed twice and incubated with 1 µg/ml of affinity-purified fluorescein isothiocyanate (FITC)-conjugated F(ab')2 anti-human IgG Fcγ-specific antibody (Tago Biosource, Camarillo, Calif.). The cells were then washed twice and fixed in 1% paraformaldehyde in PBS. For monoclonal antibody saturation assessment, platelets were incubated in 100 µl PBS with various serial dilutions of antibody for 0.5 h, washed and incubated with 1 µg/ml FITC-conjugated F(ab')2 anti-mouse IgG (Cedarlane, Hornby, ON). Ten thousand events were acquired and analyzed by a FACSor™ flow cytometer (Becton-Dickinson, San Jose, Calif.) operating at 15 mW power. Background staining was assessed by comparison with serum obtained from each animal prior to any manipulation.

For the steric hindrance studies, HLA-A2 positive PBLs were incubated with saturating levels of 1) alloantibody-containing Hu-PBL-SCID sera or 2) monoclonal HLA antibody for 1 h at room temp. After washing twice with PBS, the cells were then incubated with 1) monoclonal HLA antibody or 2) Hu-PBL-SCID sera respectively. Following washing, cells from 1) were incubated with goat F(ab')2 anti-mouse IgG-FITC, and cells from 2) were incubated with goat F(ab')2 anti-human IgG-FITC. Cells were then analyzed by flow cytometry.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for inhibiting an HLA alloimmune response to platelet transfusion, said method comprising the steps of:

presensitizing platelets with at least one monoclonal antibody, or an F(ab')$_2$ fragment thereof, against HLA Class I or a β2-microglobulin;

b) transfusing the presensitized platelets of step a) into a patient, said presensitized platelets inhibiting an HLA alloimmune response in said patient.

2. The method of claim 1, wherein said HLA alloimmune response is still inhibited after at least two transfusions into said patient.

3. A method for inhibiting refractoriness to subsequent transfusions in an alloimmunized patient, comprising the steps of:

presensitizing platelets with at least one monoclonal antibody, or an F(ab')$_2$ fragment thereof, against HLA Class I or a β2-microglobulin;

b) transfusing the alloimmunized patient with the presensitized platelets of step a), the presensitized platelets preventing refractoriness to the transfusion.

* * * * *